United States Patent
Mehta et al.

(10) Patent No.: US 12,370,136 B2
(45) Date of Patent: *Jul. 29, 2025

(54) AQUEOUS SUSPENSION SUITABLE FOR ORAL ADMINISTRATION

(71) Applicant: LIQMEDS WORLDWIDE LIMITED, Weedon (GB)

(72) Inventors: Sandip P. Mehta, Ahmedabad (IN); Henil Alpeshbhai Patel, Ahmedabad (IN); Jayanta Kumar Mandal, Ahmedabad (IN)

(73) Assignee: LIQMEDS WORLDWIDE LIMITED, Weedon (GB)

( * ) Notice: Subject to any disclaimer, the term of this patent is extended or adjusted under 35 U.S.C. 154(b) by 0 days.

This patent is subject to a terminal disclaimer.

(21) Appl. No.: 18/944,456

(22) Filed: Nov. 12, 2024

(65) Prior Publication Data

US 2025/0064726 A1  Feb. 27, 2025

Related U.S. Application Data

(63) Continuation of application No. 18/426,972, filed on Jan. 30, 2024, now Pat. No. 12,168,069, which is a continuation of application No. 18/300,504, filed on Apr. 14, 2023, now Pat. No. 11,925,704, which is a continuation of application No. 17/824,993, filed on May 26, 2022, now Pat. No. 11,654,106, which is a continuation of application No. 16/308,731, filed as application No. PCT/IB2017/053348 on Jun. 7, 2017, now Pat. No. 11,369,567.

(30) Foreign Application Priority Data

Jun. 8, 2016 (IN) .............................. 201621019719

(51) Int. Cl.
| | | |
|---|---|---|
| A61K 9/00 | (2006.01) | |
| A61K 9/10 | (2006.01) | |
| A61K 31/366 | (2006.01) | |
| A61K 31/40 | (2006.01) | |
| A61K 31/505 | (2006.01) | |
| A61K 47/02 | (2006.01) | |
| A61K 47/10 | (2017.01) | |
| A61K 47/14 | (2017.01) | |
| A61K 47/22 | (2006.01) | |
| A61K 47/24 | (2006.01) | |
| A61K 47/26 | (2006.01) | |
| A61K 47/38 | (2006.01) | |
| A61K 47/40 | (2006.01) | |

(52) U.S. Cl.
CPC .......... *A61K 9/0053* (2013.01); *A61K 9/0095* (2013.01); *A61K 9/10* (2013.01); *A61K 31/366* (2013.01); *A61K 31/40* (2013.01); *A61K 31/505* (2013.01); *A61K 47/02* (2013.01); *A61K 47/10* (2013.01); *A61K 47/14* (2013.01); *A61K 47/22* (2013.01); *A61K 47/24* (2013.01); *A61K 47/26* (2013.01); *A61K 47/38* (2013.01); *A61K 47/40* (2013.01)

(58) Field of Classification Search
CPC ...................................................... A61K 31/40
See application file for complete search history.

(56) References Cited

U.S. PATENT DOCUMENTS

| | | | |
|---|---|---|---|
| 2003/0191192 A1 | 10/2003 | Venus et al. | |
| 2004/0235935 A1 | 11/2004 | Vanderbist | |
| 2007/0116758 A1 | 5/2007 | Dlugatch et al. | |
| 2008/0260837 A1 | 10/2008 | Namburi et al. | |
| 2009/0311330 A1 | 12/2009 | Driver | |
| 2012/0270933 A1 | 10/2012 | Phelps et al. | |

FOREIGN PATENT DOCUMENTS

| | | |
|---|---|---|
| CN | 101637452 B | 5/2011 |
| WO | 2002100394 A1 | 12/2002 |
| WO | 2007125339 A1 | 11/2007 |
| WO | 2010098906 A1 | 9/2010 |
| WO | 2017212409 A1 | 12/2017 |

OTHER PUBLICATIONS

European Search Report issued in Patent Application No. EP 17737639.9-1109; Mailing Date: Mar. 2, 2021; 40 pages.
First Examination Report issued in India Application No. 201621019719; Mailing Date: Nov. 12, 2020; 6 pages.
Remington's Pharmaceutical Science (1980), pp. 202-203 and 294-310 ("Remington's").
QPharma's Low Solubility Actives and Chemical Abstract Monographs for QPharma's Low Solubility Actives, 2021 ("QPharma's Low Solubility Actives"); 29 pages.
Surfactants, Particle Sciences Drug Development Series, Technical Brief 2010 vol. 1 ("Surfactants Technical Brief"); 2 pages.
Dow's Methocel Cellulose Ethers Technical Handbook (2002) ("Methocel Handbook"); 32 pages.
The Keltrol®/Kelzan® Xanthan Gum Book (2008) by CP Kelco ("Xanthan Gum Book"); 32 pages.
Handbook of Pharmaceutical Excipients, 6th Edition (2009), pp. 110-114 and 549-553 ("Handbook"); 15 pages.
Joshi et al., Differentiation of 3-Hydroxy-3-methylglutaryl-coenzyme A Reductase Inhibitors by Their Relative Lipophilicity, Pharm. Pharmacol. Commun. (1999) 5: 269-271.
Zaid et al., Compounding and stability evaluation of atorvastatin extemporaneous oral suspension using tablets or pure powder, Eur. J. Hosp. Pharm. (2017) 24: 157-161 (published online on Jun. 15, 2016; doi: 10.1136/ejhpharm-2016-000913).

*Primary Examiner* — Bong-Sook Baek
(74) *Attorney, Agent, or Firm* — Merchant & Gould P.C.; Daniel R. Evans

(57) ABSTRACT

The present invention provides liquid oral dosage form of lipid lowering agent suitable for oral administration to human or animals.

13 Claims, No Drawings

AQUEOUS SUSPENSION SUITABLE FOR ORAL ADMINISTRATION

RELATED APPLICATIONS

This application is a continuation of U.S. patent application Ser. No. 18/426,972, filed on Jan. 30, 2024, now U.S. Pat. No. 12,168,069, which is a continuation of U.S. patent application Ser. No. 18/300,504, filed on Apr. 14, 2023, now U.S. Pat. No. 11,925,704, which is a continuation of U.S. patent application Ser. No. 17/824,993, filed on May 26, 2022, now U.S. Pat. No. 11,654,106, which is a continuation of U.S. patent application Ser. No. 16/308,731, filed on Dec. 10, 2018, now U.S. Pat. No. 11,369,567, which is the U.S. national stage application of PCT/IB2017/053348, filed on Jun. 7, 2017, which claims priority to Indian Patent Application number 201621019719, filed on Jun. 8, 2016, the subject matter of each application is incorporated by reference.

FIELD OF THE INVENTION

The present invention is related to liquid oral dosage form of lipid lowering compound preferably statin products suitable for oral administration.

BACKGROUND OF THE INVENTION

Statins are HMG-CoA reductase inhibitors, a class of drug used to lower the cholesterol level by inhibiting HMG-CoA reductase. Currently available in the market either as tablets, capsules, or solutions for injection. An individual may have difficulty swallowing the usual solid dosage form, and daily injections are difficult to administer. For children, dose management is difficult if tablet to cut or crush because of no accuracy of dose. Based on that a patent application US20120270933 claims liquid solution comprising statin and at least one solubilizer with statement that liquid statin formulation are not available due to poor solubility or insolubility Still using solubilizer there is an increase in the unknown impurity. So to avoid this in the present invention solubilizer is avoided.

OBJECT OF INVENTION

The primary objective of present invention is to provide liquid oral dosage form of lipid lowering compound.

Another objective of present invention is to provide oral suspension/solution having dose flexibility for patients who need special doses of the drug and have difficulties in swallowing oral dosage forms.

Still another objective of present invention is to provide oral suspension/solution with improved taste having high patient compliance.

It is yet another objective of present invention to provide process of preparation of oral suspension/solution of statin products suitable for oral administration.

It is yet another objective of present invention to provide oral suspension/solution of atorvastatin products suitable for oral administration and process for preparation thereof without use of stabilizer and buffering agent.

SUMMARY OF THE INVENTION

The present invention provides liquid oral dosage form of lipid lowering agent, statin suitable for oral administration to human or animals. These formulations are useful for administration of the lowest dose of statin for treatment of high cholesterol level and any diseases due to high cholesterol. This liquid oral dosage form formulation statins include atorvastatin, simvastatin, rosuvastatin etc. a preferred is atorvastatin.

DETAILED DESCRIPTION OF THE INVENTION

The present invention relates to suspension of statin products suitable for oral administration to humans or animals.

Statins are HMG-CoA reductase inhibitors, used for the treatment of high cholesterol level or any disease due to high cholesterol level in human and animals. Currently available doses of statins are either as tablets, capsules, or solutions for injection. Present invention is liquid oral dosage form of statin for oral administration without use of solubilizer and/or a stabiliser such as an antioxidant. Formulation of present invention is useful even to administer the lowest dose of the composition.

This liquid oral dosage form formulation statins include atorvastatin, simvastatin, rosuvastatin etc. wherein preferred is atorvastatin.

Statins are known for poor aqueous solubility and stability but present invention provides dosage form without use of stabilizer, buffering agent and optionally solubilizer.

Common formula of present invention comprises statin between of 0.1 and 5% and at least one suspending agent between 0.2 and 6%. In addition the composition comprises viscosity modifier, sweetener, flavors, colors, preservatives and water.

In a preferred form of present invention excipients used can be selected from vehicle, co-solvent, preservative, sweetener, chelating agent, buffer, flavoring agent and sweetness/flavor enhancing agent.

Vehicles used in pharmaceutical formulations are mainly liquid bases which carries drugs and other excipients in dissolved or dispersed state. Pharmaceutical vehicles are of two types: 1) Aqueous vehicles; 2) Oily vehicles.

Aqueous vehicles can be selected from but not limited to purified water, hydro-alcoholic, polyhydric alcohols and buffers, while oily vehicles can be selected from vegetable oils, oils, organic oily bases or emulsified bases.

Co-solvents are used to increase solubility of drugs that show low solubility in water. It is also used to improve viscosity, taste and flavor. Co-solvent system comprises of solvents selected from but not limited to propylene glycol, glycerin, alcohol, polyhydric alcohol and water for injection which is used alone or in combination.

Preservatives are included in pharmaceutical solutions to control the microbial bioburden of the formulation having broad spectrum of antimicrobial activity, must be chemically and physically stable over the shelf-life of the product and have low toxicity. Preservative can be selected from group but not limited to alcohol, benzyl alcohol, chlorobutol, chlorocresol, alkyl esters of paraben, phenol, phenyl ethanol, sodium benzoate, antimicrobial solvents like propylene glycol, chloroform.

Sweetener can be selected from but not limited to sucrose, liquid glucose, glycerol, sorbitol, saccharin sodium, sucrose and aspartame to impart sweetness to the formulation.

Chelating agent is used for drug stabilization, to maintain potency of active ingredients and to stabilize colors and flavors. Chelating agent can be selected from but not limited to citric acid monohydrate, disodium edetate, dipotassium edetate, edetic acid, fumaric acid, malic acid, phosphoric acid, sodium edetate, tartaric acid and trisodium edetate.

pH of the formulation is between 5 and 10 can be controlled and optimize the physicochemical performance of the formulation by using base or buffer can be selected from but not limited to sodium acetate, sodium hydroxide, sodium citrate, sodium phosphate and disodium phosphate.

Flavouring agents are mainly use to increase the palatability and enhance the aesthetic qualities of the formulation. Flavouring agent can be selected but not limited to oil based flavouring agent such as essential oils including peppermint oil, orange oil, lemon oil etc.

In aspect of present invention, oral pharmaceutical solution of atorvastatin is formulated which comprises of an active ingredient, atorvastatin and other excipients selected from vehicle, co-solvent, preservative, sweetener, chelating agent, buffer, flavouring agent and sweetness/flavour enhancing agent, wherein pH of formulation is maintained between 5 and 10, more particularly between 6 and 9.

Oral liquid composition without use of stabilizer, buffering agent and optionally solubilizer can be oral suspension or oral solution.

EXAMPLES

The present invention can be described by way of example or strategy only. It is to be recognized that modifications falling within the scope and spirit of the description or claims, which would be obvious to a person skilled in the art based upon the disclosure herein, are also considered to be included within the scope of this disclosure.

Composition is general for oral liquid dosage form of statin is as under:

| Sr. No. | Ingredients for Statin Oral Solution | Range (% w/w) |
|---|---|---|
| 1. | Active Ingredient | 2-10% |
| 2. | Solubilizer | 0.0-15% |
| 3. | Co-solvent | 0.0-15% |
| 4. | Suspending agent | 0.0-10% |
| 5. | Complexing agent | 0-5% |
| 6. | Sweetner | 0-50% |
| 7. | Flavor | 0.0-2% |
| 8. | Surfactant | 0.0-0.2% |
| 9. | Vehicle | 0.0-95% |

For the composition of atorvastatin 1 mg/ml, drug and excipients with its range are shown below in table:

Strategy I & II: With Antioxidant and Without Antioxidant

| Sr. No. | Ingredients | STRATEGY I 20 mg/5 ml | STRATEGY II 20 mg/5 ml |
|---|---|---|---|
| 1 | Atorvastatin | 20.00 | 20.00 |
| 2 | Propylene Glycol | 250.00 | 250.00 |
| 3 | Carboxymethyl cellulose sodium | 33.33 | 33.33 |
| 4 | Magnesium Aluminium silicate | 66.67 | 66.67 |
| 5 | Butylatedhydroxyanisole | 0.00 | 2.00 |
| 6 | Purified water | qs 5 ml | qs 5 ml |

Manufacturing Process for (Strategy I)

1. Sodium Carboxymethyl Cellulose were slowly added in 30% W/W purified water and stir well till clear solution was obtained.

2. Dispensed quantity of Magnesium Aluminium silicate was added in step 1, additional 20% w/w a purified water add in Step 1 and stir well till all solid mass was get mixed properly i.e. homogeneously dispersed.

3. API was added into propylene glycol and mixed properly where solubilizer was used. This mixture was added in to step 2 and stirred through simple stirrer properly to get homogenized suspension.

4. Add 50% w/w of remaining purified water for makeup the suspension.

Manufacturing Process for (Strategy II)

1. Sodium Carboxymethyl Cellulose were slowly added in 30% W/W purified water and stir well till clear solution was obtained.

2. Dispensed quantity Magnesium Aluminium silicate was added in STEP 1, additional 20% w/w a purified water add in Step 1 and stir well till all solid mass was get mixed properly at i.e. homogeneously dispersed RPM (600-800).

3. BHA and API was added into propylene glycol and mixed properly where solubilizer was used. This mixture was added in to step 2 and stirred through simple stirrer properly to get homogenized suspension.

4. Add remaining purified water for makeup the suspension

Result achieved for strategy I and II based on stability are as under:

| | Trial | | | | | |
|---|---|---|---|---|---|---|
| | Strategy I | | | Strategy II | | |
| | Stability condition | | | | | |
| | Initial | 25° C./60% RH | 40 C./75% RH | Initial | 25° C./60% RH | 40° C./75% RH |
| Impurity A | 0.05% | 0.02% | 0.02% | 0.05% | 0.02% | 0.05% |
| Impurity C | 0.01% | ND | ND | ND | ND | ND |
| Impurity D | 0.02% | 0.01% | 0.01% | 0.03% | 0.01% | 0.01% |
| Lactone | 0.03% | 0.1% | 0.06% | 0.04% | 0.05% | 0.05% |
| Ester | ND | ND | ND | ND | ND | ND |
| Unknown Impurities | 0.08% (RRT 0.74) | 0.15 % (RRT 0.80) | 1.40% (RRT 0.80) | 0.12% (RRT 0.74) | 0.63% (RRT 0.80) | 1.10% (RRT 0.80) |
| Total Impurities | 0.53% | 0.42% | 2.1% | 0.42% | 1.00% | 1.7% |

Conclusion

On based of 3M 25° C./60% RH, impurity profile of Strategy I & Strategy II, antioxidant having no effective role.

Based on the results achieved with or without use of stabilizer, we have also tried for avoiding buffering agent as described in strategy III and IV along with avoiding stabilizing agent.

Strategy III & IV: With Buffering Agent Without Buffering Agent

| Sr. No. | Ingredients for Atorvastatin Oral Suspension | STRATEGY III 20 mg/5 ml | STRATEGY IV 20 mg/5 ml |
|---|---|---|---|
| 1. | Atorvastatin | 20.00 | 20.00 |
| 2. | Carboxymethyl cellulose sodium | 33.33 | 33.33 |
| 3. | Magnesium Aluminium silicate | 66.66 | 66.66 |
| 4. | Sucralose | 50.00 | 50.0 |
| 5. | Acesulfame K | 5.00 | 5.0 |
| 6. | Methyl parahydroxybenzoate | 5 | 5 |
| 7. | Ethyl parahydroxybenzoate | 1 | 1 |
| 8. | Potassium Di-Hydrogen Phosphate | 0.959 | — |
| 9. | Di-potassium Hydrogen Phosphate | 0.078 | — |
| 10. | Orange flavour | 15.0 | 15.0 |
|  | Purified water | Up to 5 ml | Up to 5 ml |

Manufacturing Process for Strategy III 1. 50% w/w Purified water was heated till the temperature reached to 80-90° C. Dispensed quantity of Methyl parahydroxybenzoate and Ethyl parahydroxybenzoate was added in to this and stirred to get clear solution. Cool down solution at room temperature.
2. Add sucralose, Acesulfame K in step 1, stir well till clear solution.
3. Sodium Carboxymethyl Cellulose were slowly added in step 1, stir well till clear viscous solution.
3. Magnesium Aluminium silicate were add in step 2 stir well till all solid mass was get mixed properly i.e. homogeneously dispersed.
4. Add and disperse Atorvastatin in 10% w/w purified water m separate vessel mix properly for 30 min, with high speed homogenization.
5. Step 4 is add in step 3, mix well through simple stirrer till get homogenized suspension.
6. Add Potassium Di-Hydrogen Phosphate, Di-potassium Hydrogen Phosphate in 20% w/w purified water, add slowly in step 5 to achieve pH 6.0-9.0
7. Add flavour in step 6.
8. Add purified water and makeup the volume.

Manufacturing Process for Strategy IV 1. 50% w/w Purified water was heated till the temperature reached to 80-90° C. Dispensed quantity of Methyl parahydroxybenzoate (E218) and Ethyl parahydroxybenzoate (E214) was added in to this and stirred to get clear solution. Cool down solution at room temperature.
2. Add sucralose, Acesulfame K in step 1, stir well till clear solution.
3. Sodium Carboxymethyl Cellulose were slowly add in step 1, stir well till clear viscous solution.
4. Magnesium Aluminium silicate were add in step 2 stir well till all solid mass was get mixed properly i.e. homogeneously dispersed.
5. Add and disperse Atorvastatin in 10% w/w purified water in separate vessel mix properly for 30 min i.e. homogeneously dispersed.
6. Step 4 is add in step 3, mix well through simple stirrer and get homogenize medium i.e. homogeneously suspension.
7. Add flavour in step 6.
8. Add purified water and makeup the volume.

The results we achieved for strategy III and IV are as under:

| | Trial | | | | | |
|---|---|---|---|---|---|---|
| | Strategy III | | | Strategy IV | | |
| | Stability condition | | | | | |
| | | 3M | | | 3M | |
| | Initial | 25° C./40% RH | 40 C./25% RH % | Initial | 25° C./40% RH | 40 C./25% RH |
| Impurity A | ND | 0.07 | 0.07 | 0.04 | 0.06 | 0.06 |
| Impurity C | ND | ND | ND | ND | ND | ND |
| Impurity D | 0.03 | 0.04 | 0.05 | 0.06 | 0.02 | 0.02 |
| Lactone | 0.05 | 0.08 | 0.11 | 0.18 | 0.1 | 0.08 |
| Ester | ND | ND | ND | ND | ND | ND |
| Unknown Impurities | 0.05 (0.81 RRT) | 0.25 (0.78 RRT) | 0.76 (0.78 RRT) | 0.07 (0.80 RRT) | 0.09 (0.79 RRT) | 0.12 (0.79 RRT) |
| Total Impurities | 0.1 | 0.62 | 1.4 | 0.57 | 0.44 | 0.44 |

Conclusion

Based on 3M 25° C./40% RH & 3M 40° C./25% RH impurity profile of Strategy III & Strategy IV, stabilizer buffering agent is having partial or no effective role.

Strategy V: For Effective Homogenization

| Sr. No. | Ingredients for Atorvastatin Oral Suspension | STRATEGY V 20 mg/5 ml |
|---|---|---|
| 1. | Atorvastatin | 20.00 |
| 2. | Carboxymethyl cellulose sodium | 33.33 |
| 3. | Magnesium Aluminium silicate | 66.66 |
| 4. | Sucralose | 50.00 |
| 5. | Acesulfame K | 5.00 |
| 6. | Methyl parahydroxybenzoate | 5 |
| 7. | Ethyl parahydroxybenzoate | 1 |
| 8. | Orange flavour | 15.0 |
| 9. | Purified water | Up to 5 ml |

Manufacturing Process for Strategy V 1. 50% w/w Purified water was heated till the temperature reached to 80-90° C. Dispensed quantity of Methyl parahydroxybenzoate (E218) and Ethyl parahydroxybenzoate (E214) was added in to this and stirred to get clear solution. Cool down solution at room temperature.
2. Add sucralose, Acesulfame K in step 1, stir well till clear solution.
3. 90% quantity of Sodium Carboxymethyl Cellulose were slowly add in step 1, stir well till clear viscous solution.
4. Magnesium Aluminium silicate were add in step 2 stir well till all solid mass was get mixed properly i.e. homogeneously dispersed.
5. In a separate vessel take 10% v/v of purified water and remaining qty of sodium carboxymethyl cellulose and disperse Atorvastatin. Homogenize through high speed for 30 min, achieve particle size d90 1 micron-15 micron.
6. Step 5 is add in step 4, mix well through simple stirrer and get homogenize medium i.e. homogeneously suspension.
7. Add flavour in step 6.
8. Add purified water to make up and homogenize through high speed for 45 min.

Trial results: Based on the homogenization trials, final formulation with different particle size distribution was evaluated with Reference marketed product (Lipitor 40 mg Film coated tablet) at a dose of 40 mg per volunteer. And the results of the bio equivalence (BE) study is as mentioned below:

astatin were found to be 67.79 and 93.60%, respectively for formulation strategy IV (homogenized product with API particle size D90=22.39 μm), which is not within acceptable range of 90.00-110.00%.

The ratios of geometric least squares means of test product (T) and reference product (R) for Ln-transformed pharmacokinetic parameters (Cmax and AUC0-t) of atorvastatin were found to be 90.08% and 98.75% respectively, which is in between range of 90.00-110.00% for formulation strategy V (homogenized product with API particle size D90=6.02 μm). Furthermore, the 90% confidence intervals for the ratio of geometric least squares means for Ln-transformed pharmacokinetic parameter AUC0-t is within the acceptable bioequivalence interval of 80.00-125.00%, while that of Cmax is not within the acceptable bioequivalence interval of 80.00-125.00% due to limited number of subjects and lower power of the study. By adding more number of subjects and higher power in the study, the 90% confidence intervals for the ratio of geometric least squares means for Ln-transformed pharmacokinetic parameter Cmax may be within the acceptable bioequivalence interval of 80.00-125.00%.

| BE STUDY I: Formulation particle size ($D_{90}$-22.39 μm) | | | | | |
|---|---|---|---|---|---|
| Pharma-cokinetic | Ln-transformed Geometric Least Squares Mean | | | 90% Confidence Interval | |
| Parameters | Test Product | Reference Product | T/R | (Parametric) | |
| (Units) | (T) | (R) | (%) | Lower | Upper |
| Cmax (ng/mL) | 36.1290 | 53.2937 | 67.79 | 52.49 | 87.56 |
| AUC0-t (ng · hr/mL) | 164.7519 | 176.0092 | 93.60 | 86.32 | 101.50 |

| BE STUDY II: Formulation particle size ($D_{90}$-6.02 μm) | | | | | |
|---|---|---|---|---|---|
| Pharma-cokinetic | Ln-transformed Geometric Least Squares Mean | | | 90% Confidence Interval | |
| Parameters | Test Product | Reference Product | T/R | (Parametric) | |
| (Units) | (T) | (R) | (%) | Lower | Upper |
| Cmax (ng/mL) | 55.6268 | 61.7538 | 90.08 | 63.43 | 127.92 |
| AUC0-t (ng · hr/mL) | 212.8483 | 215.5457 | 98.75 | 82.91 | 117.61 |

Conclusion

Based on above data, (a) stabilizer and buffering agent have partial or no effective role and (b) suitable particle size of API in finished product to get bioequivalent product, can be achieved from effective homogenization Observation From Study 2

The ratios of geometric least squares means of test product (T) and reference product (R) for Ln-transformed pharmacokinetic parameters (Cmax and AUC0-t) of atorv- From the study it was concluded that effective homogenization-particle size reduction method is required to produce the product having comparative pharmacokinetic profile to Innovator product (Lipitor).

The same strategy and manufacturing process can be applicable to all HMG-CoA reductase inhibitors like simvastatin, rosuvastatin.

Further, formulation trials were also tried for atorvastatin oral solution without using stabilising and buffering agent. Few strategies are mentioned below:

Atorvastatin Oral Solution

| Sr. No. | Ingredients for Atorvastatin Oral Solution | STRATEGY | | | |
|---|---|---|---|---|---|
| | | I 20 mg/5 ml | II 20 mg/5 ml | III 20 mg/5 ml | IV 20 mg/5 ml |
| 1. | Atorvastatin | 20.00 | 20.0 | 20.0 | 20.00 |
| 2. | Propylene glycol | 250 | — | 150 | — |
| 3. | Ethanol | — | — | 5% v/v | 20% v/v |
| 4. | HPBCD | — | — | — | 400 |
| 5. | Sorbitol solution | 300 | 300 | 300 | 300 |
| 6. | Peppermint flavor | 0.5 | 0.5 | — | 0.5 |
| 7. | Orange flavor | — | 0.5 | 0.5 | — |
| 8. | Polysorbat 80 | 1 | 3 | — | — |
| 9. | Glycerine | Up to 5 ml | — | — | Up to 5 ml |
| 10. | Purified water | — | Up to 5 ml | Up to 5 ml | — |

Manufacturing Process Strategy I

1. Add atorvastatin in Propylene glycol mix well till clear solution obtained.
2. Add sorbitol solution in 50% v/v of total quantity of glycerine mix well to obtain homogeneous mixture.
3. Add step 2 in to step 1 mix well.
4. Add polysorbate 80 in step 3 to obtain clear viscous solution.
5. Add peppermint in step 4 and mix well till homogeneous solution obtained.
6. Make up the volume with glycerine pH of solution (4.0-7.0)

Manufacturing Process Strategy II

1. Add atorvastatin in purified water mix well than add polysorbate 80 and mix well till clear solution obtain.
2. Add sorbitol solution in Step 1 stir well till clear solution.
3. Add Orange flavor in step 2 stir well till clear solution.
4. Make up the volume with purified water pH of solution (5.0-9.0)

Manufacturing Process Strategy III

1. Add atorvastatin in ethanol mix well in separate vessel.
2. Add propylene glycol in step 1 till clear solution obtain.
3. Add sorbitol solution in 50% purified water in separate vessel mix well to obtain homogeneous mixture
4. Add Orange flavor in step 3 stir well till clear solution.
5. Step 1 add in step 4 stir well till clear solution obtain.
6. Make up the volume with purified water. Ph of solution (5.0-8.0)

Manufacturing Process Strategy IV

1. Add atorvastatin in ethanol mix well in separate vessel.
2. Add HPBCD in step 1 stir well till complete complex is formed.
3. Add sorbitol solution in 50% purified water in separate vessel mix well to obtain homogeneous mixture.
4. Add peppermint flavor in step 3 stir well till clear solution.
5. Step 1 add in step 4 stir well till clear solution obtain.
7. Make up the volume with glycerine. pH of solution (4.0-7.0)

The same strategy can be applicable to all other HMG-CoA reductase inhibitors like simvastatin, rosuvastatin, etc.

The invention claimed is:

1. An aqueous suspension for oral administration, comprising:
    atorvastatin in an amount of about 4 mg/ml;
    a suspending agent in an amount of about 2% w/w comprising carboxymethyl cellulose sodium in an amount of about 0.7% w/w and magnesium aluminum silicate in an amount of about 1.3% w/w;
    one or more pharmaceutically acceptable excipients selected from the group consisting of a co-solvent, a preservative, a sweetener, a buffer, and a flavoring agent;
    and
    a vehicle comprising water;
    wherein the atorvastatin has a d90 particle size of from 1 μm to 15 μm and the suspension does not contain a solubilizer and a stabilizer.

2. The aqueous suspension of claim 1, wherein atorvastatin is present in an amount of 4 mg/mL.

3. The aqueous suspension of claim 1, wherein the preservative is present in an amount of from 0.01% w/w to 0.5% w/w.

4. The aqueous suspension of claim 1, wherein the co-solvent is selected from the group consisting of alcohol, glycerin, a polyhydric alcohol, propylene glycol, and a combination thereof.

5. The aqueous suspension of claim 1, wherein the preservative is selected from the group consisting of benzyl alcohol, chlorobutol, chlorocresol, an alkyl ester of paraben, phenol, phenyl ethanol, sodium benzoate, and a combination thereof.

6. The aqueous suspension of claim 1, wherein the preservative is selected from the group consisting of benzyl alcohol, chlorobutol, chlorocresol, an alkyl ester of paraben, phenol, phenyl ethanol, sodium benzoate, propylene glycol, chloroform, and a combination thereof and the preservative is present in an amount of from 0.01% to about 0.5% w/w.

7. The aqueous suspension of claim 1, wherein the preservative comprises an alkyl ester of paraben.

8. The aqueous suspension of claim 1, wherein the preservative comprises an alkyl ester of paraben in an amount of from 0.01% to about 0.5% w/w.

9. The aqueous suspension of claim 1, wherein the sweetener is selected from the group consisting of sucrose, glucose, glycerin, sorbitol, saccharin sodium, sucralose, aspartame, acesulfame potassium, and a combination thereof.

10. The aqueous suspension of claim 1, wherein the sweetener is selected from the group consisting of sucrose, glucose, glycerin, sorbitol, saccharin sodium, sucralose, aspartame, acesulfame potassium, and a combination thereof and the sweetener is present in an amount of from about 0.1% w/w to about 2% w/w.

11. The aqueous suspension of claim 1, wherein the flavoring agent is present in an amount of from 0.01 to 2.0% w/w.

12. The aqueous suspension of claim 1, wherein the pH of the aqueous suspension ranges from 5 to 10.

13. The aqueous suspension of claim 1, wherein the pH of the aqueous suspension ranges from 6 to 9.

* * * * *